United States Patent [19]

Jaeb et al.

[11] Patent Number: 4,880,304
[45] Date of Patent: Nov. 14, 1989

[54] OPTICAL SENSOR FOR PULSE OXIMETER

[75] Inventors: Jonathan P. Jaeb; Dennis W. Gilstad; Ronald L. Branstetter, all of San Antonio, Tex.

[73] Assignee: Nippon Colin Co., Ltd., Komaki, Japan

[21] Appl. No.: 33,406

[22] Filed: Apr. 1, 1987

[51] Int. Cl.⁴ .................... G01N 33/49; A61B 5/00
[52] U.S. Cl. ................................... 356/41; 128/633
[58] Field of Search .................. 356/39, 40, 41, 409, 356/414, 446; 250/343; 128/633

[56] References Cited

U.S. PATENT DOCUMENTS

| | | | |
|---|---|---|---|
| 3,910,701 | 10/1975 | Henderson et al. | 356/39 |
| 3,922,090 | 11/1975 | Fain | 356/407 X |
| 4,086,915 | 5/1978 | Kofsky et al. | 356/41 X |
| 4,167,331 | 9/1979 | Nielsen | 356/41 X |
| 4,447,150 | 5/1984 | Heinemann | 356/41 |
| 4,451,530 | 5/1984 | Kaule et al. | 356/71 X |
| 4,484,819 | 11/1984 | Ulrich | 356/446 |
| 4,586,513 | 5/1986 | Hamaguri | 356/41 X |
| 4,624,572 | 11/1986 | van den Bosch | 356/446 X |

OTHER PUBLICATIONS

Takatani et al. "A Noninvasive Tissue Reflectance Oximeter" Annals of Biomedical Engineering, vol. 8, No. I, pp. 1-15 (1980).

Primary Examiner—Vincent P. McGraw
Attorney, Agent, or Firm—Matthews & Branscomb

[57] ABSTRACT

An improved optical sensor which has increased sensitivity and which is resistant to the effects of ambient light. In one embodiment of the invention, the sensor housing has a flat lower face with a central protrusion in which a plurality of light emitting diodes and an optical sensor are mounted. When the sensor is placed on the patient's tissue, the portion of the sensor face containing the LEDs and detector protrudes slightly into the tissue to provide improved optical coupling of the sensor to the skin. A light absorbing compliant material is attached to the perimeter of the sensor to reduce the effects of ambient light and to provide a cushion to minimize discomfort to the patient. In an alternate embodiment of the sensor, the LEDs and detector are mounted in a horizontal configuration substantially parallel to the surface of the tissue. The light produced by the LEDs is projected into a central chamber of the housing where the respective beams are combined and directed toward the tissue. In this emodiment, the desired combining of the beams can be achieved through the use of a set of mirrors or a prism. Various combinations of the improvements provided by each of the embodiments described above can be incorporated into either a transmission or backscatter optical sensor to provide a compact, sensitive optical sensor which is resistant to interference caused by ambient light.

5 Claims, 5 Drawing Sheets

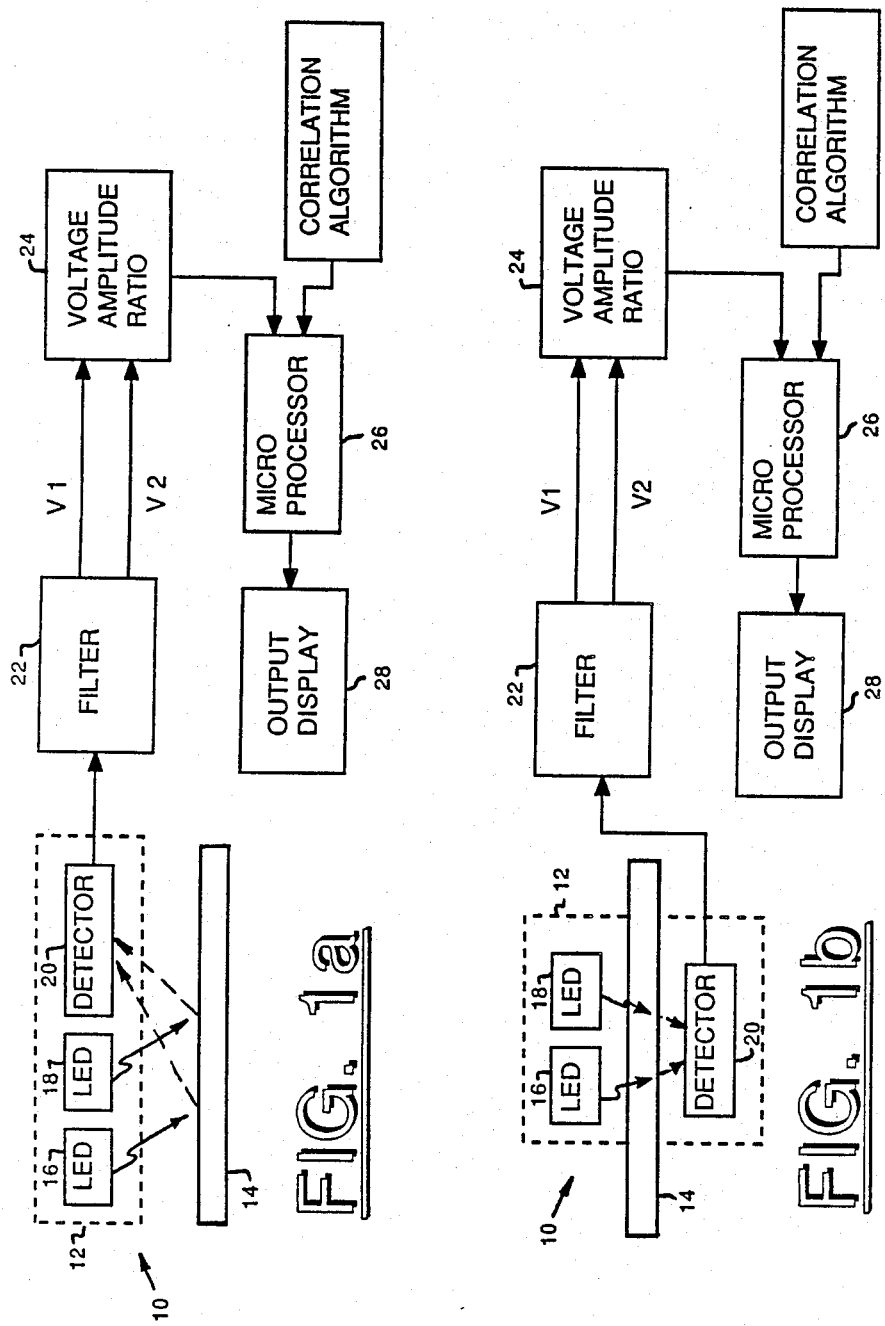

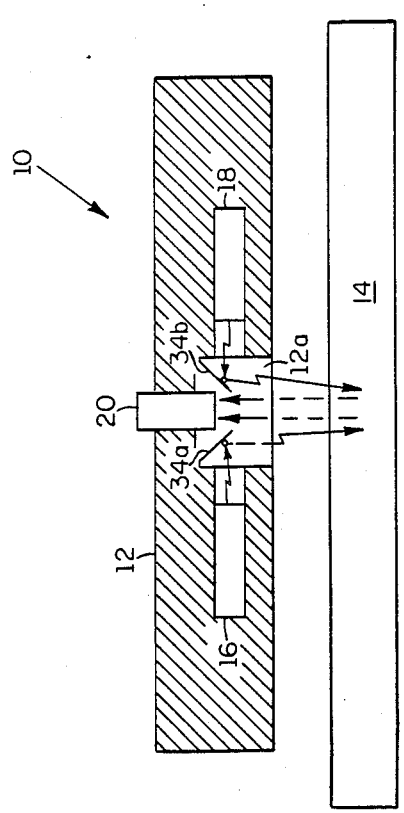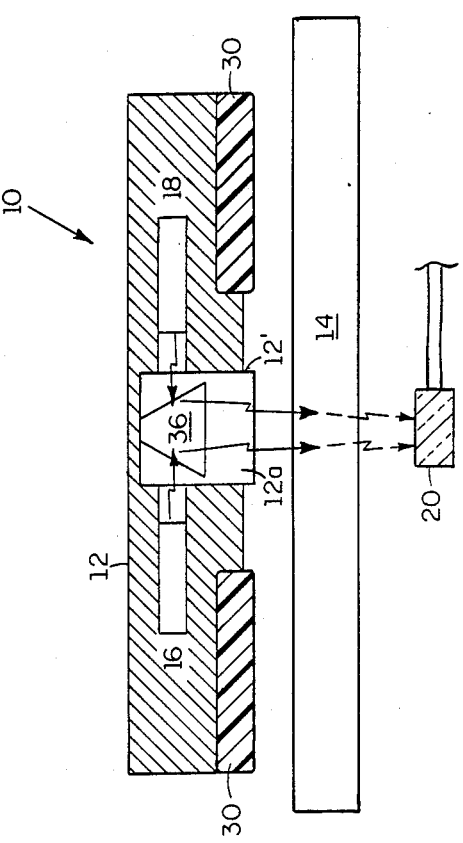
FIG. 4a
FIG. 4b

OPTICAL SENSOR FOR PULSE OXIMETER

FIELD OF THE INVENTION

The present invention relates generally to optical sensors used in biomedical applications. Specifically, the present invention provides an improved optical sensor which can be used in conjunction with monitoring equipment used to estimate the degree of oxygen saturation in blood. The sensor of the present invention has increased sensitivity and is resistant to interference due to ambient light.

BACKGROUND

In many clinical situations, it is extremely important to be able to obtain continuous measurements of a patient's tissue oxygenation. One of the most common methods for measuring blood oxygen saturation requires removal and analysis of a sample of the patient's blood. Analysis of an actual sample of blood is still considered the most accurate method for obtaining a reading of absolute blood oxygen saturation. However, this method is undesirable in cases where it is necessary to monitor blood oxygen saturation over long periods of time. While it is desirable to have an absolute measure of blood oxygen saturation, it is often sufficient to measure relative changes in the saturation. For example, in the operating room, the physician is typically concerned only with significant changes in the patient's blood oxygen saturation, and is less concerned with the measurement of absolute saturation. In this situation, a noninvasive oximeter which is capable of detecting significant changes in the blood oxygen content would be especially useful.

Hemoglobin oxygen saturation (OS) of blood is defined as the ratio of the oxyhemoglobin ($HbO_2$) concentration to the total hemoglobin (Hb) concentration. It is well known that hemoglobin and oxyhemoglobin have different optical absorption spectra and that this difference in absorption spectra can be used as a basis for an optical oximeter. Specifically, the difference between the absorption spectra for red and infrared light can be used to determine blood oxygen saturation. Most of the currently available oximeters using optical methods to determine blood oxygen saturation are based on transmission oximetry. These devices operate by transmitting light through an appendage such as a finger or an earlobe. By comparing the characteristics of the light transmitted into one side of the appendage with that detected on the opposite side, it is possible to compute oxygen concentrations. The main disadvantage of transmission oximetry is that it can only be used on portions of the body which are thin enough to allow passage of light.

There has been considerable interest in recent years in the development of an oximeter which is capable of using reflected light to measure blood oxygen saturation. A reflectance oximeter would be especially useful for measuring blood oxygen saturation in portions of the patient's body which are not well suited to transmission measurements. Experimental results suggest that it is possible to obtain accurate indications of blood oxygen content through the use of reflectance techniques.

One of the most common optical sensors for oximeters employs a plurality of optical fibers for directing light to and from the tissue. These sensors tend to be relatively expensive and they are bulky and fragile. In addition, optical fibers have a high transmission loss, thus requiring higher power sources or very sophisticated amplifying circuitry to obtain a usable signal.

A number of other problems have been encountered in prior art optical sensors used in noninvasive oximetry systems. For example, it is often difficult to obtain sufficient signal strength for transmitted or reflected light in the red spectrum. Another common problem experienced with prior art optical sensors is interference caused by ambient light entering at the perimeter of the sensor housing. In addition to the problems discussed above, prior art sensors tend to have an inherent inaccuracy associated with the spacing of the light sources in the sensor housing. Since the spacing of the sensors causes different portions of the underlying tissue to be illuminated with the light produced by the respective LED, the light detected by the optical detector necessarily represents the oxygen saturation at different locations in the tissue.

Various methods and apparati for utilizing the optical properties of blood to measure blood oxygen saturation have been shown in the patent literature. Representative devices for utilizing the transmission method of oximetry have been disclosed in U.S. Pat. Nos. 4,586,513; 4,446,871; 4,407,290; 4,226,554; 4,167,331; and 3,998,550. In addition, reflectance oximetry devices and techniques are shown generally in U.S. Pat. Nos. 4,447,150; 4,086,915; and 3,825,342.

Numerous other works have disclosed theoretical approaches for analyzing the behavior of light in blood and other materials. The following is a brief list of some of the most relevant of these references: "New Contributions to the Optics of Intensely Light-Scattering Materials, Part 1," by Paul Kubelka, *Journal of the Optical Society of America*, Volume 38, No. 5, May 1948; "Optical Transmission and Reflection by Blood," by R.J. Zdrojkowski and N.R. Pisharoty, *IEEE Transactions on Biomedical Engineering*, Vol. BME-17, No. 2, April 1970; and "Optical Diffusion in Blood," by Curtis C. Johnson, *IEEE Transactions on Biomedical Engineering*, Vol. BME-17, No. 2, April 1970.

The effectiveness of noninvasive oximetry systems such as those described above could be significantly enhanced by an improved optical sensor. Specifically, there is a need for an optical sensor having increased sensitivity and increased resistance to the effects of ambient light.

SUMMARY OF THE INVENTION

The present invention overcomes the difficulties of the prior art by providing an improved optical sensor which has increased sensitivity and which is resistant to the effects of ambient light. In one embodiment of the invention, the sensor housing has a flat lower face with a central protrusion in which a plurality of light emitting diodes and an optical sensor are mounted in a vertical configuration. When the sensor is placed on the patient's tissue, the portion of the sensor face containing the LEDs and detector protrudes slightly into the tissue. This feature provides a more repeatable coupling effect between the face of the sensor and the tissue and increases the sensitivity of the sensor. A light absorbing compliant material is attached to the perimeter of the sensor to reduce the effects of ambient light and to provide a cushion to minimize discomfort to the patient.

In an alternate embodiment of the sensor, the LEDs and detector are mounted in a horizontal configuration substantially parallel to the surface of the tissue. The light produced by the LEDs is projected into a central chamber of the housing where the respective beams are combined and directed toward the tissue. In this embodiment, the desired combining of the beams can be achieved through the use of a set of mirrors or a prism.

Various combinations of the improvements provided by each of the embodiments described above can be incorporated into either a transmission or backscatter optical sensor to provide a compact, sensitive optical sensor which is resistant to interference caused by ambient light.

BRIEF DESCRIPTION OF THE DRAWINGS

FIG. 1a is a schematic block diagram of a simplified embodiment of a noninvasive blood oxygen saturation monitoring system using a backscatter optical sensor.

FIG. 1b is a schematic block diagram of a simplified embodiment of a noninvasive blood oxygen saturation monitoring system using a transmissive optical sensor.

FIG. 4a is an elevational side view of an alternate embodiment of the sensor of the present invention having the LEDs mounted in a horizontal configuration and the optical detector mounted in a vertical configuration.

FIG. 4b is an elevational side view of an alternate embodiment of the sensor of the present invention having the LEDs and the optical detector mounted in a horizontal configuration.

DETAILED DESCRIPTION OF THE PREFERRED EMBODIMENT

Figure 2B:
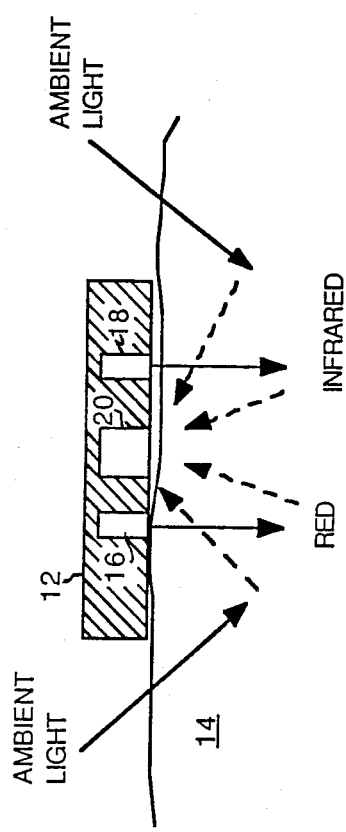
FIG. 2b is an elevational side view of the sensor of FIG. 2a showing the effects of ambient light entering from the perimeter of the sensor housing.

Referring to the drawings in more detail, and to FIGS. 1a and 1b in particular, simplified schematic block diagrams are shown of noninvasive measurement systems for determining blood oxygen saturation. The two systems are essentially identical, except for the type of optical sensor. In the system shown in FIG. 1a, a reflectance optical sensor 10 is employed, while the system of FIG. 1b employs a transmission optical sensor 10'. In the following discussion these two types of optical sensors will be identified generally by the reference number 10, although it is to be understood that the improvements provided by the various embodiments of the present invention can be incorporated into either backscatter or transmission type sensors. Indeed, the improvements provided by the optical sensor of the present invention are not limited to oximetry measurements, but can be applied in virtually any application requiring a highly sensitive optical sensor which is resistant to the effects of ambient light.

Referring to FIGS. 1a and 1b, a sensor 10 is shown positioned over a portion of the patient's tissue 14 such that light produced by two light emitting diodes (LED) 16 and 18 will be reflected by (or transmitted through) arterial blood in the tissue and detected by a photodetector 20. In the preferred embodiment, the LED 16 emits light having a wavelength of 600 nm (red) and the LED 18 emits light having a wavelength of 800 nm (infrared). However, the invention is not intended to be limited to any specific wavelength of light produced by the above-mentioned LEDs. Proper operation of the invention requires only that one source of light having a wavelength for which the absorption coefficients of hemoglobin and oxyhemoglobin are approximately equal and that the second source of light have a wavelength for which these absorption coefficients differ from one another. In an alternate embodiment of the invention, each of the LEDs could be replaced with an appropriate source of laser radiation providing monochromatic light at the desired wavelengths.

The output of the photodetector 20 will be an electrical signal representing a combination of direct-current (DC) and alternating-current (AC) components of the light reflected by (or transmitted through) the arterial blood in the tissue 14. This output signal is processed by an appropriate filter 22 to produce signals corresponding to the AC voltage components of each of the wavelengths of incident light. These AC voltage signals are then processed by a voltage amplitude ratio circuit 24 which provides a voltage amplitude ratio signal to the microprocessor 20. The microprocessor processes the voltage amplitude ratio of the AC voltage signals in accordance with a correlation algorithm to obtain an indication of blood oxygen saturation which is displayed on the display 28.

The functional features of the above-described system components can be accomplished thorough the use of electronic components and techniques which are well known in the art. For example, U.S. Pat. No. 4,447,150, issued to Heinemann, which by this reference is incorporated for all purposes, shows a system for illuminating a sample of blood with light at two wavelengths and for detecting light signals reflected by the blood. In addition, a system for obtaining electrical representations of the AC components of the reflected signals is shown in U.S. Pat. No. 4,586,513, issued to Hamaguri, which by this reference is incorporated for all purposes.

Figure 2A:
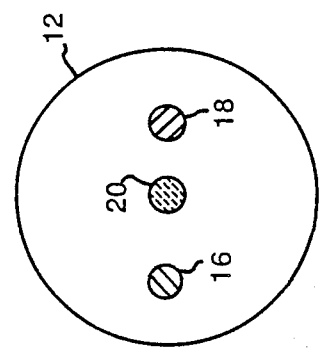
FIG. 2a is a bottom view of a typical backscatter optical sensor showing details relating to the spacing of the LEDs in relation to the optical detector.

FIG. 2a is a bottom view of a typical optical sensor 10 used in backscatter oximetry systems. The sensor consists of a disc-shaped housing 12 having a flat lower face which is placed on the surface of the tissue, as shown in FIG. 2b. The lower face of the housing 12 contains LEDs 16 and 18 which emit light in the red and infrared specta, respectively, and an optical sensor 20 for detecting light reflected by subsurface tissue The sensor design shown in FIGS. 2a and 2b presents a number of problems related to signal strength and susceptibility to interference. The red light signal transmitted through or reflected by the tissue 14 is typically much weaker than the signal corresponding to light in the infrared spectrum. In systems employing one red LED, therefore, it is necessary to intermittently overdrive this LED beyond its maximum continuous power rating. This tends to shorten the life of the LED and can cause slight shifts in the wavelength of the emitted light.

Another problem with the sensor design shown in FIGS. 2a and 2b is interference caused by ambient light entering from the perimeter of the sensor housing.

Figure 3B:
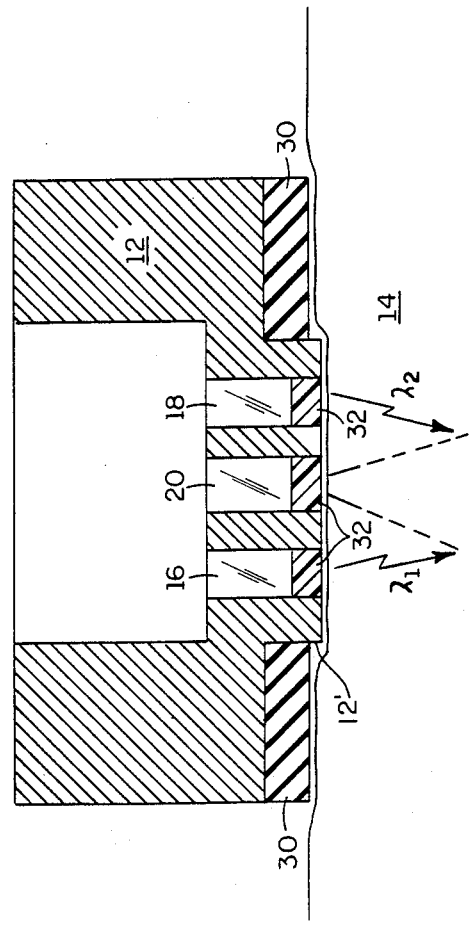
FIG. 3b is an elevational side view of the optical sensor of FIG. 3a showing details relating to the light absorbing pad and the mounting of the LEDs.
Figure 3A:
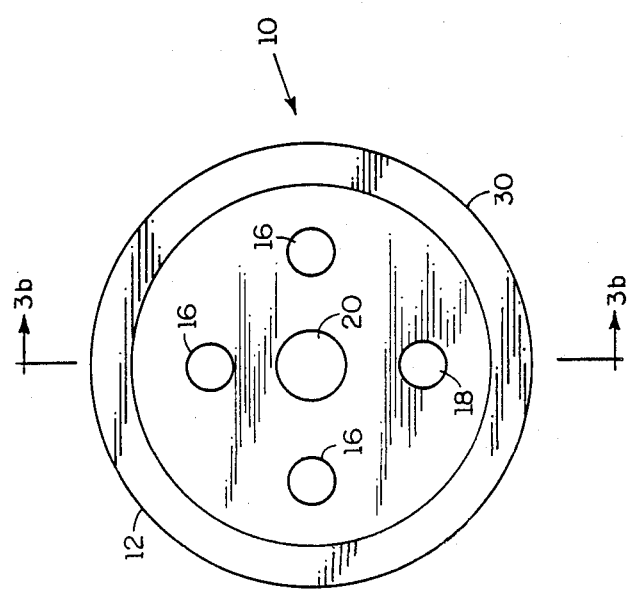
FIG. 3a is a bottom view of a preferred embodiment of the improved optical sensor for use with a backscatter pulse oximeter.

One embodiment of an optical sensor which overcomes the difficulties discussed above is shown in FIGS. 3a and 3b. The problem of low signal strength is solved by placing a total of four LEDs in a radial pattern around the optical detector 20. In this embodiment, three red LEDs and one infrared LED are mounted in the lower face of the sensor. These LEDs are mounted in central protrusion 12' in the lower face of the sensor housing 12. When the sensor housing is pressed against the surface of the tissue, as shown in FIG. 3a, the portion of the sensor face containing the LEDs and the optical detector protrudes into the tissue slightly, thereby increasing the signal strength of the detected signal. Interference due to ambient light entering from the edges of the sensor is reduced by a compliant, light absorbing pad 30 attached to the perimeter of the lower face of the sensor. This pad also provides a cushion to reduce discomfort to the patient. Interference due to ambient light is further reduced by recessing the LEDs 16, 18 and the detector 20 within the housing and by coating the respective LEDs with a polymer sealant 32. The coating provides improved optical index matching and also provides an electrical and biological seal between the sensor and the tissue.

In addition to the two problems discussed above, the sensor shown in FIGS. 2a and 2b tends to be inherently inaccurate because of the spacing of the LEDs 16 and 18 in relation to the detector 20. Ideally, the light produced by each of the LEDs should illuminate the same portion of the tissue 14 underlying the sensor to ensure accurate calculation of the voltage amplitude ratio for the reflected (or transmitted light). A second embodiment of the present invention for solving this problem is shown in FIGS. 4a and 4b. In this embodiment, the LEDs 16 and 18 are mounted in a horizontal configuration with the light beams from the LEDs directed into a central chamber 12a in the housing. The light beams are combined in the chamber 12a and are directed toward the tissue by an appropriate optical guide. For example, in FIG. 4a, the light beams emitted by LEDs 16 and 18 are directed toward the skin by reflectors 34a and 34b. The reflectors are spaced such that light reflected by the tissue 14 can pass therebetween to be detected by detector 20. In FIG. 4b, the beams emitted by the LEDs are directed toward the tissue 14 by a prism 36. In this illustration, the detector 20 is shown in the opposite side of the tissue 14. This embodiment could easily be modified, however, to operate as a reflectance sensor with the detector contained in the housing 12. In addition, either of the embodiments can be modified to incorporate the protruding lower face 12' and the compliant light absorbing pad 30.

Figure 5B:
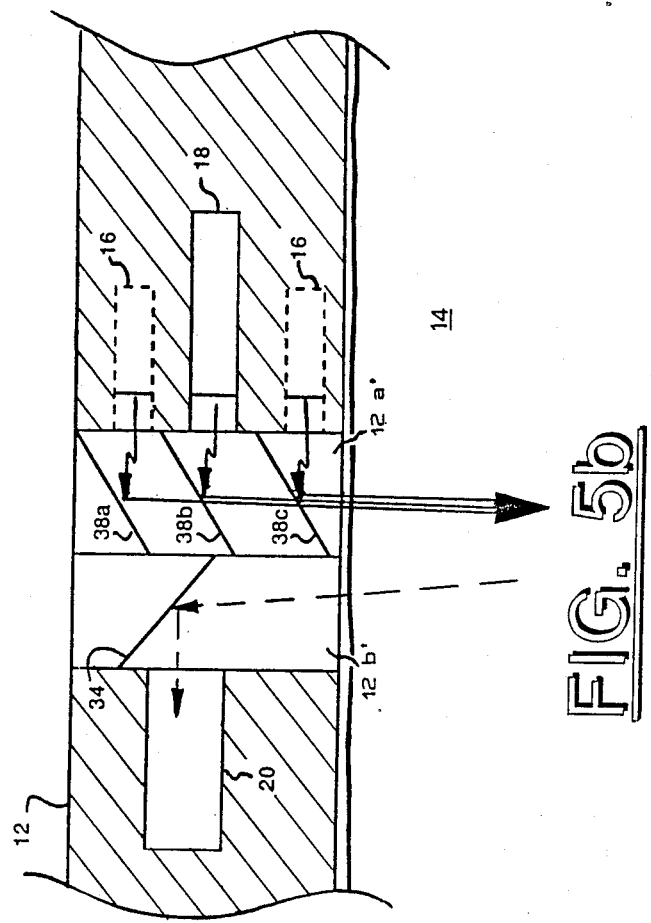
FIG. 5b is a cross-sectional side view taken along lines 5b—5b of FIG. 5a, showing details relating to the half-silvered mirrors used to combine the beams emitted by the light sources.
Figure 5A:
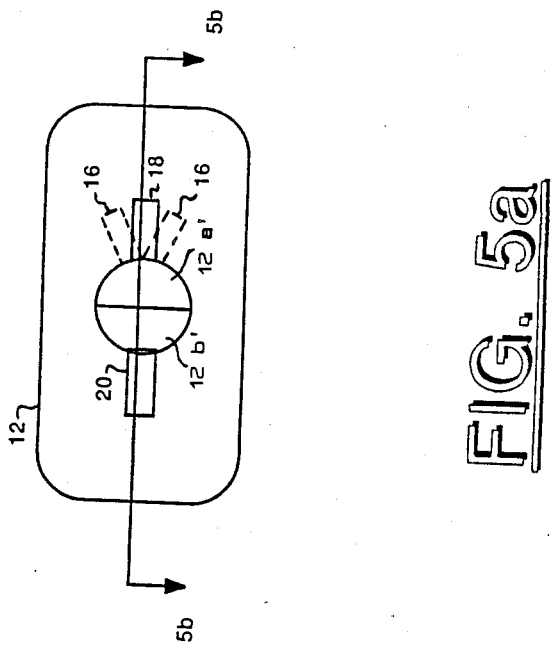
FIG. 5a is a top view of an alternate embodiment of the present invention showing details relating to the overlapping, staggered configuration for mounting the light sources in the housing.

The horizontal mounting configuration of the LEDs shown in FIGS. 4a and 4b provides an extremely compact profile for the sensor. The dimensions of the sensor can be further reduced by mounting the LEDs in the vertically overlapping staggered configuration shown in FIGS. 5a and 5b. In this embodiment, the beams from the various LEDs are directed toward a chamber 12a' where they are combined and directed toward the tissue 14 by mirror 38a and by half-silvered mirrors 38b, and 38c, shown in FIG. 5b. Light emitted by upper LED 16' is reflected downward by the mirror 38a and passes through half-silvered mirrors 38b and 38c. Similarly, the light emitted by LED 18 is reflected by half-silvered mirror 38b and passes through half-silvered mirror 38c. Finally, the light emitted by LED 16 is reflected downward by half-silvered mirror 38. The various beams emitted by the LEDs are thus combined to form a composite beam which illuminates the same portion of the underlying tissue 14. Light reflected by the tissue 14 is received in the chamber 12b' and is directed toward the optical detector 20 by the reflector 34.

While the optical sensor of the present invention has been described in connection with the preferred embodiment, it is not intended to be limited to the specific form set forth herein, but on the contrary, it is intended to cover such alternatives, modifications and equivalents as may be reasonably included within the spirit and scope of the invention as defined by the appended claims

We claim:

1. An optical sensor, comprising:
   a housing, said housing having a general flat lower surface with a central protrusion extending a predetermined distance from said lower surface, said protrusion adapted to provide an optical couple between said sensor and the surface of a patient's tissue;
   a first source of light at a first wavelength for which the absorption coefficients of hemoglobin and oxyhemoglobin are approximately equal and a second source of light at a second wavelength for which said absorption coefficients differ from one another, said first and second sources of light mounted in said central protrusion extending from said lower surface;
   light detecting means mounted in said protrusion of said housing to detect light at said first and second wavelengths after contact with arterial blood; and
   light absorbing means on said lower surface of said housing surrounding said central protrusion for preventing the transmission of ambient light between the lower surface of said housing and said tissue.

2. The optical sensor according to claim 1, said first light source comprising at least one light emitting diode emitting light in the infrared spectrum, said second light source comprising at least two light emitting diodes emitting light in the red spectrum.

3. The optical sensor according to claim 2, said first light emitting diode producing light at approximately 660 nanometers, said second light emitting diode producing light at approximately 800 nanometers.

4. The optical sensor according to claim 3, each said light emitting diode being recessed in the lower face of said protrusion, defining a plurality of generally cylindrical chambers in the lower face said protrusion, each of said chambers being filled with a polymer sealant.

5. The optical sensor according to claim 4, said means for absorbing light comprising a compliant, light absorbing pad attached to the lower face of said housing along the perimeter thereof.

* * * * *